United States Patent
Greene et al.

(10) Patent No.: US 10,495,626 B2
(45) Date of Patent: Dec. 3, 2019

(54) WOOD MARKING AND IDENTIFICATION

(71) Applicant: Troy Corporation, Florham Park, NJ (US)

(72) Inventors: Richard Wayne Greene, Altamonte Springs, FL (US); Barry Dean Haugen, Valencia, CA (US); Stephen Edward Cavender, Edison, NJ (US)

(73) Assignee: Troy Corporation, Florham Park, NJ (US)

( * ) Notice: Subject to any disclaimer, the term of this patent is extended or adjusted under 35 U.S.C. 154(b) by 466 days.

(21) Appl. No.: 15/143,316

(22) Filed: Apr. 29, 2016

(65) Prior Publication Data

US 2017/0168038 A1   Jun. 15, 2017

Related U.S. Application Data

(60) Provisional application No. 62/265,822, filed on Dec. 10, 2015.

(51) Int. Cl.
| | | |
|---|---|---|
| *G01N 33/46* | (2006.01) | |
| *B27K 3/08* | (2006.01) | |
| *B27K 3/22* | (2006.01) | |
| *C09D 5/14* | (2006.01) | |
| *C09D 5/18* | (2006.01) | |
| *B27K 3/50* | (2006.01) | |

(52) U.S. Cl.
CPC ............ *G01N 33/46* (2013.01); *B27K 3/08* (2013.01); *B27K 3/22* (2013.01); *B27K 3/50* (2013.01); *C09D 5/14* (2013.01); *C09D 5/18* (2013.01)

(58) Field of Classification Search
CPC . G01N 33/46; B27K 3/08; B27K 3/22; B27K 3/50

USPC .......................................................... 428/541
See application file for complete search history.

(56) References Cited

U.S. PATENT DOCUMENTS

| | | | |
|---|---|---|---|
| 4,921,280 A | 5/1990 | Jalon | |
| 6,045,656 A | 4/2000 | Foster | |
| 6,217,794 B1 | 4/2001 | Neal | |
| 6,506,794 B1 | 1/2003 | Sianawati et al. | |
| 7,498,005 B2 * | 3/2009 | Yadav | B82Y 30/00 |
| | | | 423/21.1 |
| 8,590,800 B2 | 11/2013 | Baque | |
| 2005/0019603 A1 | 1/2005 | Kathirgamanathan | |
| 2009/0321660 A1 | 12/2009 | Samuel | |
| 2010/0152287 A1 | 6/2010 | Uhr | |
| 2014/0147691 A1 | 5/2014 | Humphrey et al. | |

FOREIGN PATENT DOCUMENTS

| | | |
|---|---|---|
| EP | 0 039 538 A1 | 11/1981 |
| WO | 2013090995 A1 | 6/2013 |

OTHER PUBLICATIONS

Non Final Office Action for U.S. Appl. No. 15/616,834, dated Nov. 16, 2018, 11 pages.
Non Final Office Action for U.S. Appl. No. 15/610,539, dated Mar. 21, 2019, 19 pages.

* cited by examiner

*Primary Examiner* — Christine T Mui
(74) *Attorney, Agent, or Firm* — RatnerPrestia

(57) ABSTRACT

Wood markers and processes for durably marking and subsequently identifying both original grain wood products and wood-plastic composite products. The wood marker can be dispersed beneath the surface of the wood, where it is protected from the elements and may endure years of exposure to the elements. The wood marker is compatible with state-of-the-art pressure-treating processes and may subsequently be detected for authentication purposes by known analytical methods.

27 Claims, No Drawings

ND IDENTIFICATION

CROSS-REFERENCE TO RELATED APPLICATIONS

This application claims priority of a provisional application entitled "WOOD MARKING AND IDENTIFICATION", which is application No. 62/265,822, filed Dec. 10, 2015, and is hereby incorporated by reference in its entirety.

BACKGROUND OF THE INVENTION

Field of the Invention

The present invention relates to a marker and a process for marking and authenticating wood products.

Description of the Related Art

Several processes for increasing the useful life of wood products by immersing the wood in liquid treating solutions are known. The treating solutions may be either aqueous or non-aqueous liquids. Pressure-vacuum cycles are commonly utilized to force the treating solutions between and into wood fibers. Manufacturers of wood products use these processes to increase the wood's resistance to weathering, microbial attack, and combustion.

Modern wood treating processes are durable, economical, and highly effective. As a result, a homeowner who invests in treated wood products or treated composite wood products to construct, for example, a wooden deck for his or her residence can reasonably expect many years of enjoyment from the wood products. In fact, lumber companies that sell treated wood frequently offer guarantees against weathering and decay that extend over ten or more years.

Now and then a treated wood product does not meet expectations. If years have passed since the wood product was purchased, it can be difficult to determine where and how the wood was treated and by whom. In these circumstances, homeowners and suppliers of treated wood products would welcome a simple and reliable method for identifying the wood products of a particular wood treating company.

Methods are known for marking and identifying products made from wood pulp, such as paper. For example, U.S. Pat. No. 4,921,820, issued to Michael Jalon, describes a process in which rare earth chelates are incorporated into extruded fibers and placed in wood pulp to make paper documents that can later be authenticated by their response to electromagnetic excitation. These methods are not practical for use with wood products, such as lumber, that are not pulped, extruded, or woven.

U.S. Pat. No. 6,045,656, issued to Foster et al., describes a method for producing anti-counterfeit paper which includes mixing dissolved florescent dye with dewatered wood fibers in a manner that loads the florescent dye into lumens of the fibers, adding the loaded fibers to a paper-making pulp, and forming the pulp into an anti-counterfeit paper. A radiation light source is employed to detect the florescent dye the anti-counterfeit paper. This method is not practical for use with wood products, such as lumber, that are not pulped, extruded or woven.

Methods are also known for marking in identifying polymeric products and coated products with florescent marking agents. For example, U.S. Pat. No. 8,590,800 B2, issued to Baque, describes methods of authenticating and identifying an article containing a chemical marking agent. The agent reportedly is inseparably enclosed in a carrier and includes selected chemical elements and or compounds as marking elements. The Baque Patent notes that metals are preferably used as marker elements, particularly elements of groups II to VI, including the subgroups I to VIII and the Periods 4 to 6. The Baque Patent explains how to incorporate the marking agent in a polymeric article or on a coated article. However, the Baque patent is silent regarding a chemical marking agent that can be inserted into wood products.

A need still exists for a marker and methods for durably marking and subsequently identifying wood products that are not pulped, extruded, or woven. A desirable marker would be placed within the wood, where it would be protected from exposure to the elements. Manufacturers of wood products would welcome a marking process that could be used in conjunction with their present wood treating processes and subsequently detected by known analytical methods.

SUMMARY OF THE INVENTION

It has now been discovered that certain carboxylates dispersed in water or an aqueous solution can be used to uniquely and durably mark wood products. The wood markers of the present invention are compatible with commercially popular processes for protecting wood products from weathering, fire, or microbial attack. The wood markers can be readily detected in the laboratory or in the field by destructive or non-destructive analytical methods.

In one aspect the invention is a composition of matter, which comprises wood and a non-biocidal metal marker. The metal has an atomic number in the range of about 12 to about 83 and may be inserted into the wood in the form of one or more carboxylates having about 6 to about 24 moles of carbon atoms per mole of the metal. Carboxylates of bismuth, cobalt, lithium, manganese, zirconium, and rare earth metals are preferred for use in the composition. Carboxylates of metals from Periods 4, 5 and 6 of the Periodic Table are especially preferred. The metal may be fluorescent when excited by x-ray radiation.

In another aspect the invention is a marker fluid dispersion for marking wood. The marker fluid dispersion comprises a continuous water or water-based pressure-treated phase; and a discrete marker phase composed of one or more non-biocidal metal carboxylates, a hydrocarbonaceous solvent, and a surfactant.

The invention is also a process for marking a wood product which includes providing a marker fluid dispersion and depositing a detectable amount of a carboxylate of a non-biocidal metal having an atomic number on the range of about 12 to about 83 in the wood product by exposing the wood product to the marker metal dispersion at greater than atmospheric pressure in order to force the carboxylate into the wood product.

The process for marking a wood product can be practiced in conjunction with a process for authenticating a wood product. The marked wood can be identified for authentication purposes by detecting the presence of the metal utilized in the carboxylate of the marker known analytical methods. For example, X-ray fluorescence analysis or plasma emission analysis can be used to detect the metal of the carboxylate.

In yet another aspect, the invention is an additive composition useful for marking wood immersed in water or in a water-based solution. The additive composition comprises a hydrocarbonaceous solvent, a bismuth carboxylate dissolved or suspended in the hydrocarbonaceous solvent, and a surfactant for dispersing the solvent and the carboxylate in water or a water-based pressure-treating solution. The bismuth carboxylate of additive composition preferably includes of about 6 to about 24 moles of carbon per mole of bismuth.

The hydrocarbonaceous solvent is preferably a petroleum distillate or a biodiesel that is capable of dissolving or suspending the carboxylate and can be dispersed in water or in water-based pressure treating fluid. The surfactant may be, for example, a nonionic surfactant, such as an alkyl polyethoxylate, or an alkyl aryl polyethoxylate. Alternatively, the surfactant may be an anionic surfactant such as an alkyl sulfate. When mixed with water, the surfactant is preferably capable of emulsifying about 50 ppm to about 1000 ppm of the hydrocarbonaceous solvent and the bismuth carboxylate in water.

DETAILED DESCRIPTION OF PREFERRED ASPECTS OF THE INVENTION

In a preferred aspect, the invention is a marked wood composition that includes wood and a marker. Although the wood may be present as a component of paper or as a component of a wood-plastic composite made of wood fibers or wood flour and a thermoplastic material, the wood is preferably lumber that has been sawn or milled from timber and retains the original wood grain substantially intact. The wood may be the product of air drying, kiln drying, or any known treating process for increasing the resistance of wood to weathering, ultra-violet degradation, combustion, fungal discoloration, or microbial infestation.

The marker is a non-biocidal metal compound or a mixture of non-biocidal metal compounds. For the present purposes, "non-biocidal metal" means a metal other than silver, copper, nickel, barium, chromium, mercury, zinc, or cadmium. "Biocidal metal" means then silver, copper, nickel, barium, chromium, mercury, zinc, or cadmium.

The metal compound is preferably a carboxylate of metal cation in which the metal selected from the group consisting of non-biocidal metals having an atomic number in the range of about 12 to about 83 and mixtures thereof, and a carboxylic anion including about 6 to about 18 carbon atoms. More preferably, the selected metal is in Period 4, Period 5, or Period 6 of the Periodic Table of the Elements as depicted on the inside front cover of Perry's Chemical Engineers' Handbook, $50^{TH}$ Edition (1984). A rare earth metal or a mixture of rare earth metals is also preferred as the selected metal. Bismuth, cobalt, lithium, manganese, zirconium, bismuth carboxylates, cobalt carboxylates, lithium carboxylates, manganese carboxylates, zirconium carboxylates, and mixtures thereof are especially preferred for use as the marker of the present invention. Ideally, the marker is fluorescent when excited by x-ray radiation.

In addition to the non-biocidal metal carboxylate, the marked wood may include one or more biocidal metals, one or more biocidal metal compounds and mixtures thereof.

The marker of the present invention is preferably inserted into the wood in the form of a metal carboxylate, more preferably a metal carboxylate that includes a metal cation and about 6 to about 18 carbon atoms per carboxylate anion. The carboxylate may be the reaction product of a metal and a mono-, di- or tri-carboxylic acid; preferably, a mono- or di-carboxylic acid; and most preferably, a di-carboxylic acid. It is preferred that the carboxylate includes about 6 to about 24 moles of carbon per mole of metal. The marker may be introduced to the wood in the form of a carboxylate and subsequently be reduced to the corresponding metal oxide or metal hydroxide on or in the wood, while remaining within the scope of the present invention.

The marker is dispersed beneath the surface of the marked wood, where it is relatively impervious to removal by rain or snow and not susceptible to degradation by sunlight. The metallic portion of the metal carboxylate, metal oxide, or metal hydroxide can be detected beneath the surface of the marked wood by known analytical methods, such as non-destructive X-Ray Fluorescence ("XRF") analyses and destructive Acid-Digestion followed by and D-C Plasma Emission ("DCP") analyses.

In addition to the non-biocidal metal, one or more biocidal metals may be present in the marked wood.

In another preferred aspect, the invention is a marker fluid dispersion for treating and marking wood. The marker fluid dispersion includes water or a water-based pressure-treating liquid phase for increasing the resistance of wood to weathering, fire, or microbial attack.

If the wood has previously been treated to resist weathering, fire, and microbial attack; or if no additional resistance to weathering, fire, or microbial attack is desired; water will suffice as the liquid phase of the marker fluid dispersion. In that case, the marker fluid dispersion may be a multi-phase dispersion in which water is a continuous liquid phase and a marker liquid phase including a carboxylate of a non-biocidal metal selected from the group consisting of non-biocidal metals having an atomic number in the range of 12 to 83 and mixtures thereof, that includes about 6 to about 18 carbon atoms per molecule; a hydrocarbonaceous solvent; and a surfactant as the disperse liquid phase.

On the other hand, one of the advantages of the present invention is that it is compatible with many of the water-based pressure-treating liquids currently in commercial use. In many cases, a known water-based pressure-treating liquids can serve as the continuous liquid phase while a marker liquid phase including a carboxylate of a non-biocidal metal selected from the group consisting of non-biocidal metals having an atomic number in the range of 12 to 83 that includes about 6 to about 18 carbon atoms per molecule; a hydrocarbonaceous solvent; and a surfactant is the disperse liquid phase. Because the pressure-vacuum cycles required for protecting and marking are similar, a single pressure-treating process can often be utilized to accomplish both goals simultaneously. Minor adjustments to the composition of the pressure-treating liquid may be necessary in some cases, but these adjustments will be apparent to and readily accomplished by pressure-treating operators. It will be appreciated that some known and commercially popular water-based pressure-treating liquids include biocidal metal, such as copper or zinc.

It is preferred that the selected non-biocidal metal for the marker fluid dispersion is in Period 4, Period 5, or Period 6 of the Periodic Table of the elements. A rare earth metal or a mixture of rare earth metals is especially preferred for use as the as the selected non-biocidal metal. Bismuth carboxylate, cobalt carboxylate, lithium carboxylate, manganese carboxylate, zirconium carboxylate or a mixture thereof are especially preferred for use as the carboxylate. In addition to the non-biocidal carboxylate, one or more biocidal metals may be present in the marker fluid dispersion.

In yet another preferred aspect, the invention is a process for marking a wood product. The process includes providing a marker fluid dispersion as described above. In the process, a detectable amount of the metal or the carboxylate from the marker fluid dispersion is deposited on and in the wood product by exposing the wood product to the marker fluid dispersion at greater than atmospheric pressure. For the present purposes, "detectable amount" means an amount that can be reliably detected by a known analytical method. It will be appreciated that the amount that can be reliably detected will depend on the analytical method. For example, a detectable amount for XRF analysis is 5 ppm or more for zirconium, and 50 ppm or more for cobalt and manganese. As another example, a detectable amount for DCP analysis is 5 ppm for zirconium and cobalt, and 1 ppm for lithium and manganese. The appropriate detectable amount will be apparent to practitioners who routinely measure the amount of metal present in wood.

Similarly, conditions of time, temperature, concentration and pressure for the marking process will be apparent to practitioners who operate water-based pressure-treating for protecting wood products. Positive pressure of about 100 psig is often applied for about one hour to wood immersed in pressure-treating solutions for protecting wood. Negative pressure of about 5 psi is often applied to wood for 30 minutes in order to draw out air from the wood.

The proportion of the carboxylate in the disperse phase should be within the range of about 10 percent to about 80 weight percent. In order to dissolve or suspend the carboxylate in the disperse phase, a surfactant such as an alkyl polyethoxylate, an alkyl aryl polyethoxylate, or an alkyl sulfate is included in the disperse phase, along with a hydrocarbonaceous solvent such as a light petroleum distillate or biodiesel.

Preferably, the wood will be exposed to the marker fluid dispersion during alternating of periods of negative pressure and positive pressure to draw air out of the wood and force the marker fluid into the wood. Preferably, the metal or the carboxylate will be dispersed beneath the surface of the wood and forced into and between individual wood cells.

In still another preferred process, the invention is a process for authenticating a wood product. The authenticating process includes marking wood by exposing it to a marker fluid dispersion as described above and subsequently identifying the wood product by detecting the presence of the selected non-biocidal metal or the selected non-biocidal carboxylate in the wood product by any conventional method.

It will be appreciated that the present invention can be used to disperse two or more selected non-biocidal metals or selected non-biocidal carboxylates simultaneously in the wood in pre-determined rations in order to make detection more certain authentication more certain or to convey a numeric or alphabetic message. The appended claims are intended to read on use of the compositions or processes of the present invention to mark and identify these ratios and messages.

In an additional aspect, the invention is an additive composition for marking wood in water or a water based pressure treating solution pressure treating solution. The additive composition includes a hydrocarbonaceous solvent, a bismuth carboxylate dissolved or suspended in the hydrocarbonaceous solvent and a surfactant for dispersing or emulsifying the solvent in water or the water based pressure treating solution.

Preferably, the carboxylate includes about 6 to about 12 moles of carbon per mole of bismuth. Petroleum distillates or biodiesels which can dissolve the bismuth carboxylate and be dispersed in water or the water based pressure treating solution pressure treating solution naphthas are suitable for use as the hydrocarbonaceous solvent. Light petroleum distillates, such as naphthas are preferred hydrocarbonaceous solvents.

Preferably the surfactant is an alkyl polyethoxylate, an alkyl aryl polyethoxylate, or an alkyl sulfate. The surfactant should be capable of emulsifying about 50 ppm to about 1000 ppm of the hydrocarbonaceous solvent and the bismuth carboxylate in water.

The following examples and procedures are presented to communicate the invention, and are not meant to limit the invention in any way. Examples described in the present tense are hypothetical examples. Unless otherwise indicated, all references to parts, percentages or proportions are based on weight.

Example 1. Inserting a Zirconium Carboxylate Marker into Southern Yellow Pine Lumber Samples of Southern Yellow Pine lumber are pressure-treated with a water-based pressure treating fluid that contains preservatives and/or fire retardants according to one of three water-based pressure treating processes known to the public as Dispersed Copper Azole ("DCA"), D-BLAZE® ("DB"), and Ecolife™ ("ECO"); except that a zirconium-based marker of the present invention is included in the pressure-treating fluid at a level of 100 ppm or 400 pm. The zirconium-based marker composition is commercially available from Troy Chemical Company of 8 Vreeland Avenue under the tradename Troychem™ Zirconium 12WD.

D-BLAZE® is a proprietary fire retardant industrial chemical for application to wood, paper, and textile fabrics, which may be used to produce Pressure-impregnated Fire Retardant Treated Wood ("FRTW"). D-BLAZE® is commercially available from Vinace, LLC LIMITED ay One Woodlawn Green, Suite 350, 200 E. Woodlawn Road, Charlotte, N.C. 28217, U.S.A.

Ecolife™ Stabilized Weather-Resistant Wood is an advanced wood protection system, utilizing a proprietary, fully integrated, wood preservative with built-in stabilizer for maximum weathering protection and enhanced performance. Ecolife™ is also commercially available from Vinace, LLC LIMITED ay One Woodlawn Green, Suite 350, 200 E. Woodlawn Road, Charlotte, N.C. 28217, U.S.A.

Pressure-treating fluid that includes a marker of the present invention will be hereinafter referred to as "Marker Fluid". The compositions of several inventive Marker Fluids are described below in Table 1.

TABLE 1

| Marker Fluid No. | Marker Fluid Name | Proprietary Mixture: D-BLAZE® ("DB") or Ecolife™ ("ECO") | Water (percent) | DCA[1] (ppm) | DDAC[2] (ppm) | CMIT + MIT[3] (ppm) | OIT[4] (ppm) | Marker[5] (ppm) |
|---|---|---|---|---|---|---|---|---|
| 1 | DCA with 100 ppm Marker | none | 98.33 | 7580 | 5920 | 326 | 328 | 100 |

TABLE 1-continued

| Marker Fluid No. | Marker Fluid Name | Proprietary Mixture: D-BLAZE® ("DB") or Ecolife™ ("ECO") | Water (percent) | DCA[1] (ppm) | DDAC[2] (ppm) | CMIT + MIT[3] (ppm) | OIT[4] (ppm) | Marker[5] (ppm) |
|---|---|---|---|---|---|---|---|---|
| 2 | DCA with 400 ppm Marker | none | 97.57 | 7580 | 5920 | 326 | 328 | 400 |
| 3 | ECO with 100 ppm Marker | ECO | May be present as components of ECO | | | | | 100 |
| 4 | ECO with 400 ppm Marker | ECO | May be present as components of ECO | | | | | 400 |
| 5 | DB with 100 ppm Marker | DB | May be present as components of ECO | | | | | 100 |
| 6 | DB with 400 ppm Marker | DB | May be present as components of ECO | | | | | 400 |

Legend
1: Dispersed copper azole (26% copper concentrate)
2: Didecyl-, Dimethyl-Ammonium Carbonate (50% active ingredient)
3: Mixture containing 5-chloro, 2-methyl-isothiazolin-3-one and 2-methyl-isothiazolin-3-one (14% active ingredients)
4: N-octyl-isothiazolinone aqueous dispersion (45% active ingredient)
5: Mixture containing dispersed zirconium carboxylates (38% active ingredients)

The samples are placed in a pressure vessel capable of withstanding positive and negative internal pressure and the vessel is sealed. A negative pressure corresponding to 15 inches of mercury vacuum gauge pressure is applied to the contents of the vessel and maintained for 4 minutes. An amount of the treating fluid sufficient to submerge the samples is introduced into the vessel. Air is introduced to equalize the internal pressure of the vessel with that of the ambient atmosphere. Eighty pounds per square inch of positive pressure is applied to the contents of the vessel and maintained for one hour.

Positive pressure within the vessel is utilized to expel the majority of liquid from the vessel. Gas is released from the vessel to reduce the internal pressure of the vessel to one atmosphere. A vacuum corresponding to 15 inches of mercury vacuum gauge pressure is applied to the contents of the vessel and maintained for 4 minutes. Air is introduced to equalize the internal pressure of the vessel with that of the ambient atmosphere, the vessel is opened, and the samples are removed from the vessel.

A hand held x-ray fluorescence analyzer is used to detect the presence of zirconium in the samples, which have been exposed to the market fluid containing the inventive marker. In each sample, the x-ray fluorescence analyzer indicates that 25 ppm of zirconium metal is present at or near a surface of the sample.

These results indicate that conventional pressure-treating fluids and associated equipment processes treating wood on a commercial scale may be modified to create new processes for inserting a durable wood marker of the present invention into wood and for identifying the source of the marked wood by confirming the presence of the marker.

Example 2 Inserting a Carboxylate Wood Marker into Commercially Obtained Lumber

In order to further demonstrate the effectiveness of the inventive processes for inserting markers into wood and detecting the presence of the marker, the following procedure was carried out repeatedly with water to which a known proportion of one of several markers of the invention had been added. In each case, the procedure inserted the respective marker of the invention into samples of Southern Yellow Pine lumber.

The samples, each 32 inches in length and having a width and thickness nominally referred to as "2×4" in the United States of America, were cut from commercially obtained eight-foot lengths of limber which had previously been pressure-treated with wood preservatives according to the well-known Micronized Coper Azole ("MCA") process, but had not been kiln dried.

The lumber samples were dried in a forced-air oven and individually weighed. The dry weight for each of the lumber samples is presented below in Table 2. Soon after weighing, six of the lumber samples were banded together with polymer spacers between layers, and placed in a vessel capable of withstanding internal pressure and internal vacuum. The vessel was sealed and a vacuum gauge pressure of 15 inches of mercury was established in the vessel for and held for five minutes.

After the five minutes of vacuum hold, the vacuum was maintained while a marking fluid containing a marker of the invention was introduced into the vessel with the lumber samples. In each case, the marking fluid contained non-anionic surfactants, hydrocarbon-based solvents, water, and one or more carboxylates of the invention. The lumber samples and marking fluid remained under this vacuum for an additional five minutes, after which the pressure in the vessel was equalized with the ambient atmosphere, increased to 100 psig of positive pressure, and maintained at 100 psig pressure for one hour.

At the end of the hour, the vessel pressure was again equalized with the ambient atmosphere and a vacuum gauge pressure of 15 inches of mercury was applied to the vessel contents and maintained for five minutes. Then the pressure in the vessel was equalized with the ambient atmosphere and the vessel was opened. The lumber samples were removed from the vessel, separated from each other, wiped dry to remove free moisture, and individually weighed. The treated weights of samples are presented below in Table 2. The difference between the dry weight and the treated weight for each sample was used to calculate a relative weight increase for each treated sample, as compared to sample's dry weight.

TABLE 2

| Sample Code | Marker in Marker Fluid (ppm) | Marker Metal and Marker Metal Content In Marker Fluid (wt%) | Dry Weight Of Sample (grams) | Treated Weight Of Sample (grams) | Weight Gain (parts Marker Fluid per million parts Dry Weight) | Weight Gain (parts Marker per million parts Dry Weight) |
|---|---|---|---|---|---|---|
| 1 | 200 | Zirconium (12) | 1391 | not applicable | not applicable | not applicable |
| 2 | 200 | Zirconium (12) | 1438 | N/A | not applicable | not applicable |
| 3 | 200 | Zirconium (12) | 1453 | N/A | not applicable | not applicable |
| 4 | 200 | Zirconium (12) | 1331 | N/A | not applicable | not applicable |
| 5 | 200 | Zirconium (12) | 1295 | N/A | not applicable | not applicable |
| 6 | 200 | Zirconium (12) | 1253 | N/A | not applicable | not applicable |
| 7 | 200 | Cobalt (6) | 2333 | 2816 | 171,520 | 34.30 |
| 8 | 200 | Cobalt (6) | 2262 | 2840 | 203,521 | 40.70 |
| 9 | 200 | Cobalt (6) | 2164 | 2729 | 207,036 | 41.41 |
| 10 | 200 | Cobalt (6) | 2005 | 2611 | 232,095 | 46.42 |
| 11 | 200 | Cobalt (6) | 1881 | 2503 | 248,502 | 49.70 |
| 12 | 200 | Cobalt (6) | 1799 | 2437 | 261,797 | 52.36 |
| 13 | 600 | Zirconium (12) | 1733 | N/A | not applicable | not applicable |
| 14 | 600 | Zirconium (12) | 1697 | N/A | not applicable | not applicable |
| 15 | 600 | Zirconium (12) | 1615 | N/A | not applicable | not applicable |
| 16 | 600 | Cobalt (6) | 2112 | 2865 | 262,827 | 157.70 |
| 17 | 600 | Cobalt (6) | 2174 | 2899 | 250,086 | 150.05 |
| 18 | 600 | Cobalt (6) | 1992 | 2824 | 294,618 | 176.77 |
| 19 | 600 | Zirconium (12) | 1707 | N/A | not applicable | not applicable |
| 20 | 600 | Zirconium (12) | 1724 | N/A | not applicable | not applicable |
| 21 | 600 | Zirconium (12) | 1737 | N/A | not applicable | not applicable |
| 22 | 600 | Cobalt (6) | 1801 | 2707 | 334,688 | 200.81 |
| 23 | 600 | Cobalt (6) | 1883 | 2715 | 306,446 | 183.87 |
| 24 | 600 | Cobalt (6) | 1916 | 2697 | 289,581 | 173.75 |
| 25 | 200 | Lithium (2) | 1765 | 2350 | 248,936 | 149.36 |
| 26 | 200 | Lithium (2) | 1686 | 2239 | 246,985 | 49.40 |
| 27 | 200 | Lithium (2) | 1771 | 2463 | 280,958 | 56.19 |
| 28 | 200 | Lithium (2) | 1662 | 2573 | 354,061 | 70.81 |
| 29 | 200 | Lithium (2) | 1679 | 2655 | 367,608 | 73.52 |
| 30 | 200 | Lithium (2) | 1591 | 2483 | 359,243 | 71.85 |
| 31 | 600 | Lithium (2) | 1463 | 1982 | 261,857 | 52.37 |
| 32 | 600 | Lithium (2) | 1514 | 2115 | 284,161 | 170.50 |
| 33 | 600 | Lithium (2) | 1540 | 2147 | 282,720 | 169.63 |
| 34 | 600 | Lithium (2) | 1723 | 2511 | 313,819 | 188.29 |
| 35 | 600 | Lithium (2) | 1647 | 2539 | 351,319 | 210.79 |
| 36 | 600 | Lithium (2) | 1530 | 2545 | 398,821 | 239.29 |
| 37 | 200 | Manganese (6) | 1749 | 2765 | 367,450 | 220.47 |
| 38 | 200 | Manganese (6) | 1615 | 2908 | 444,635 | 88.93 |
| 39 | 200 | Manganese (6) | 1669 | 2915 | 427,444 | 85.49 |
| 40 | 200 | Manganese (6) | 2007 | 2882 | 303,609 | 60.72 |
| 41 | 200 | Manganese (6) | 1819 | 2581 | 295,234 | 59.05 |
| 42 | 200 | Manganese (6) | 1809 | 2758 | 344,090 | 68.82 |
| 43 | 600 | Manganese (6) | 1703 | 2400 | 290,417 | 58.08 |
| 44 | 600 | Manganese (6) | 1682 | 2393 | 297,117 | 178.27 |
| 45 | 600 | Manganese (6) | 1545 | 2283 | 323,259 | 193.96 |
| 46 | 600 | Manganese (6) | 2094 | 2952 | 290,650 | 174.39 |
| 47 | 600 | Manganese (6) | 2022 | 2980 | 321,477 | 192.89 |
| 48 | 600 | Manganese (6) | 2011 | 2837 | 291,153 | 174.69 |

Inspection of the data presented above in Table 2 indicates that in the range of about 0.2 to 0.5 weight percent of the respective marker fluid was retained in each of the treated samples, based on the dry weight of the sample. Unless the marker is preferentially retained or preferentially rejected by the sample, this amount of marker fluid corresponds to marker retention in the range of about 30 to about 200 parts per million, based on the dry weight of the sample. This amount of marker, evenly if uniformly distributed throughout the sample, is detectable by modern analytical methods.

Example 3 Identifying the Presence of the Metal from the Carboxylate Wood Marker In order to further demonstrate the effectiveness of the inventive processes for inserting markers into wood and detecting the presence of the markers, the amount of certain residual metals in the 48 treated wood samples described above in Example 2 was quantitatively determined by non-destructive X-Ray Fluorescence ("XRF") analyses and confirmed by Acid-Digestion and D-C Plasma Emission ("DCP") analyses. The metals of interest were cobalt, lithium, manganese, and zirconium. Each of these metals was present as a carboxylate in the respective marker that had been forced into the sample by a pressure-and-vacuum process, as described above in Example 2.

A Shinadzu EDX-700 energy dispersive X-Ray Fluorescence spectrometer was used to obtain the XRF data presented below in Table 3. The treated samples described above in 2 were prepared for XRF analysis by cutting them into relatively small pieces (of about 20 mm in their greatest dimension) which would fit in a sample holder of the XRF instrument.

Exposing the sample to X-Ray radiation caused the sample to fluoresce in a spectrum that includes peak wavelengths, which are characteristic of specific elements present in the sample. The wavelengths and energy-levels of the peaks are specific to the identity of the elements in the samples; the intensities of the peaks reflects the concentration the elements in the sample. A two-point calibration for XRF analysis was performed using the marker of interest and an actual lot assay for the marker in order to avoid any potential matrix and inter-element effects.

A Beckman SpectraSpan-V Multi-Element D-C Plasma Emission Spectrometer was used to obtain the DCP data presented below in Table 3. DCP was employed to measure the concentration of the metals of interest in the treated samples. A high-temperature argon plasma was used to excite the atoms of all metals present in a sample solution, causing the metals to emit light specific and discrete wavelength ranges. A high-resolution optical spectrometer was employed to collect emitted light in specific wavelength ranges associated with the metal of interest. The energy for that wavelength range was compared with an NIST-Traceable Calibration Standard to determine the concentration of the metal in the sample.

The XRF results and the DCP results are presented in Table 3 below. Results designated "Surface Metal" refer to the concentration of the metal at or within about 1 mm inside of a surface which was exposed directly to the Marker Fluid. Results designated "15 mm Metal" provide information about the concentration of the metal of interest within about 15 to about 16 mm inside of a surface which was exposed directly to the Marker Fluid.

TABLE 3

| Sample Code | Marker Fluid Dose (ppm) | Marker Metal and Marker Metal Content In Marker Fluid (wt %) | Surface Metal by XRF (ppm) | Surface Metal by DCP (ppm) | 15 mm Metal By XRF (ppm) | 15 mm Metal By DCP (ppm) |
|---|---|---|---|---|---|---|
| 1 | 200 | Zirconium (12) | less than 25 | 27.7 | not applicable | less than 5 |
| 2 | 200 | Zirconium (12) | less than 25 | 44.8 | not applicable | 12.7 |
| 3 | 200 | Zirconium (12) | 110 | 83.8 | not applicable | 25.9 |
| 4 | 200 | Zirconium (12) | less than 25 | 36.9 | not applicable | less than 5 |
| 5 | 200 | Zirconium (12) | 125 | 106.6 | not applicable | 31.2 |
| 6 | 200 | Zirconium (12) | 90 | 77.3 | not applicable | 14.1 |
| 7 | 200 | Cobalt (6) | less than 50 | 44.2 | less than 50 | less than 5 |
| 8 | 200 | Cobalt (6) | 80 | 73.4 | less than 50 | 15.5 |
| 9 | 200 | Cobalt (6) | 120 | 112.1 | 50 | 25.3 |
| 10 | 200 | Cobalt (6) | less than 50 | 34.8 | less than 50 | 5.7 |
| 11 | 200 | Cobalt (6) | 95 | 88.3 | less than 50 | 17.6 |
| 12 | 200 | Cobalt (6) | less than 50 | 29.5 | less than 50 | less than 5 |
| 13 | 600 | Zirconium (12) | 280 | 242.8 | 80 | 57.3 |
| 14 | 600 | Zirconium (12) | 210 | 187.6 | 35 | 29.1 |
| 15 | 600 | Zirconium (12) | 300 | 270.5 | 60 | 40.5 |
| 16 | 600 | Cobalt (6) | less than 50 | 121.2 | less than 50 | 18.2 |
| 17 | 600 | Cobalt (6) | 350 | 329.8 | 110 | 88.5 |
| 18 | 600 | Cobalt (6) | 310 | 285.1 | 65 | 52.4 |
| 19 | 600 | Zirconium (12) | 365 | 333.6 | 65 | 62.3 |
| 20 | 600 | Zirconium (12) | 290 | 264.3 | 40 | 34.2 |
| 21 | 600 | Zirconium (12) | 405 | 339.7 | 55 | 44.6 |
| 22 | 600 | Cobalt (6) | 440 | 410.7 | 85 | 74.3 |
| 23 | 600 | Cobalt (6) | 370 | 323.6 | 50 | 61.6 |
| 24 | 600 | Cobalt (6) | 395 | 350.9 | less than 50 | less than 5 |
| 25 | 200 | Lithium (2) | not applicable | 17.6 | not applicable | less than 1 |
| 26 | 200 | Lithium (2) | not applicable | 39.8 | not applicable | 7.8 |
| 27 | 200 | Lithium (2) | not applicable | 24.7 | not applicable | less than 1 |
| 28 | 200 | Lithium (2) | not applicable | 12.9 | not applicable | less than 1 |
| 29 | 200 | Lithium (2) | not applicable | 42.4 | not applicable | 4.5 |
| 30 | 200 | Lithium (2) | not applicable | 33.1 | not applicable | less than 1 |
| 31 | 600 | Lithium (2) | not applicable | 110.3 | not applicable | 15.4 |
| 32 | 600 | Lithium (2) | not applicable | 60.8 | not applicable | 5.9 |
| 33 | 600 | Lithium (2) | not applicable | 43.4 | not applicable | 4.1 |
| 34 | 600 | Lithium (2) | not applicable | 96.5 | not applicable | 8.3 |
| 35 | 600 | Lithium (2) | not applicable | 77.1 | not applicable | 12.1 |
| 36 | 600 | Lithium (2) | not applicable | 52.2 | not applicable | 2.7 |
| 37 | 200 | Manganese (6) | less than 50 | 127.9 | not applicable | less than 1 |
| 38 | 200 | Manganese (6) | less than 50 | 245.2 | not applicable | 66.3 |
| 39 | 200 | Manganese (6) | less than 50 | 88.9 | not applicable | less than 1 |
| 40 | 200 | Manganese (6) | less than 50 | 164.7 | not applicable | 38.9 |
| 41 | 200 | Manganese (6) | less than 50 | 52.3 | not applicable | less than 1 |
| 42 | 200 | Manganese (6) | less than 50 | 135.8 | not applicable | less than 1 |
| 43 | 600 | Manganese (6) | 160 | 88.9 | not applicable | 21.6 |
| 44 | 600 | Manganese (6) | less than 50 | 37.0 | not applicable | 2.3 |
| 45 | 600 | Manganese (6) | less than 50 | 21.8 | not applicable | less than 1 |
| 46 | 600 | Manganese (6) | 110 | 59.3 | not applicable | 11.3 |
| 47 | 600 | Manganese (6) | less than 50 | 44.7 | not applicable | 7.7 |
| 48 | 600 | Manganese (6) | less than 50 | 31.8 | not applicable | 2.9 |

The limit DCP limit of detection is 5 ppm for zirconium and cobalt, and 1 ppm for lithium and manganese. Over these limits, inspection of Table 3 indicates that results for Surface Metal by DCP detection of wood are consistent and reliable. It can be seen that concentration of metal at the surface of the samples is generally higher than the concentration of metal in the respective Marker Fluid. Also, Table 3 shows that the concentration of metal 15 mm inside of the surface which was exposed to the respective Marker is less than the surface concentration, but generally more than the DCP limit of detection for the metal.

With the exception of lithium, the data in Table 3 indicates that the XRF results for the treated samples correlate with the DCP results. The XRF limit of detection is 25 ppm for zirconium, and 50 ppm for cobalt and manganese. Above these limits, most of the reported XRF results for zirconium, cobalt, and manganese are within about 10 percent of the reported DCP results. Lithium fluoresced weakly and is not recommended as a wood marker for detection by XRF.

Based on these results, it is reasonable to conclude that carboxylates of lithium, manganese, cobalt, or zirconium; when combined with appropriate non-aqueous solvents and non-ionic surfactants; can be utilized in a pressure-treating process for marking wood and later detecting the presence of the marker by previously known analytical methods such as XRF or DCP. By analogy, it is apparent that the pressure-treating processes may be extended to mark and identify wood by inserting one or more of many carboxylates into the wood.

Example 4, Inserting and Identifying a Bismuth Carboxylate Wood Marker in Lumber Amphiphilic bismuth carboxylate was formulated with a hydrocarbonaceous solvent and non-ionic and anionic surfactants to produce a Marker that contained 24 weight percent bismuth. The Marker was blended with water to produce a Marker Fluid that included 200 ppm of Marker. The marker Fluid was placed in a retort with wood samples. The retort was closed and heated to simulate a water-based pressure-treating process. The bismuth contents of the sample were subsequently determined by XRF analyses and by DCP analyses, as described above in Example 3. The results of these analyses are presented below in Table 4.

In Table 4, results designated "Surface Metal" refer to the concentration of bismuth at or within about 1 mm inside of a surface which was exposed directly to the Marker Fluid. Results designated "15 mm Metal" provide information about the concentration of bismuth within about 15 to about 16 mm inside of a surface which was exposed to the Marker Fluid, as described above in Example 2.

TABLE 4

| Sample Code | Marker Fluid Dose (ppm) | Marker Metal and Marker Metal Content In Marker Fluid (wt %) | Surface Metal by XRF (ppm) | Surface Metal by DCP (ppm) | 15 mm Metal By XRF (ppm) | 15 mm Metal By DCP (ppm) |
|---|---|---|---|---|---|---|
| 49 | 200 | Bismuth (24)* | 30 | 35.7 | less than 5 | 3.6 |
| 50 | 200 | Bismuth (24)* | 50 | 45.6 | 10 | 7.2 |
| 51 | 200 | Bismuth (24)* | 35 | 38.1 | less than 5 | 2.9 |
| 52 | 200 | Bismuth (24)* | 75 | 72.9 | 15 | 8.9 |
| 53 | 200 | Bismuth (24)* | 110 | 121.3 | 25 | 24.7 |
| 54 | 200 | Bismuth (24)* | 90 | 85.4 | 20 | 11.3 |

Legend
*Contains ionic surfactant and non-ionic surfactant

The above Examples are intended to better communicate the invention, and do not limit the invention in any way. The invention is defined solely by the appended claims.

U.S. Pat. No. 4,921,820, issued to Michael Jalon; U.S. Pat. No. 6,045,656, issued to Foster et al.; and U.S. Pat. No. 8,590,800 B2 are each incorporated by reference in their entirety, and specifically for their teachings regarding marketing of wood products.

What is claimed is:

1. A composition suitable for marking wood, comprising:
   (a) a continuous phase comprising water; and
   (b) a dispersed phase dispersed in the continuous phase and comprising:
      (i) at least one metal carboxylate, including an ion of a metal selected from the group consisting of non-biocidal metals having an atomic number of 12 to 83 and a carboxylate anion having 6 to 18 carbon atoms,
      (ii) at least one hydrocarbonaceous solvent, and
      (iii) at least one surfactant.

2. The composition of claim 1, wherein the metal is in Period 4, Period 5, or Period 6 of the Periodic Table of the Elements.

3. The composition of claim 1, wherein the metal comprises at least one rare earth metal.

4. The composition of claim 1, wherein the metal carboxylate is selected from the group consisting of a bismuth carboxylate, cobalt carboxylate, lithium carboxylate, manganese carboxylate, zirconium carboxylate, and mixtures thereof.

5. The composition of claim 1, wherein the metal carboxylate is a bismuth carboxylate.

6. The composition of claim 1, wherein the metal carboxylate is a zirconium carboxylate.

7. The composition of claim 1, further comprising at least one biocidal metal, biocidal metal compound, or a mixture thereof.

8. The composition of claim 7, wherein the biocidal metal is selected from the group consisting of silver, copper, nickel, barium, chromium, mercury, zinc, cadmium and mixtures thereof.

9. The composition of claim 1, wherein the continuous phase is water-based and suitable for pressure-treating wood to increase the resistance of the wood to at least one of weathering, fire, or microbial attack.

10. The composition of claim 1, wherein the metal carboxylate consists of the metal cation and the carboxylate anion.

11. The composition of claim 1, wherein the metal carboxylate is fluorescent when excited by x-ray radiation.

12. The composition of claim 1, wherein the hydrocarbonaceous solvent is a light petroleum distillate or a bio-diesel.

13. The composition of claim 1, wherein the surfactant is a nonionic surfactant.

14. The composition of claim 1, wherein the surfactant is an alkyl polyethoxylate, an aryl polyethoxylate or an alkyl sulfate.

15. The composition of claim 1, wherein the carboxylate is the anion of a mono-, di- or tri-carboxylic acid.

16. The composition of claim 1, wherein the carboxylate is the anion of di-carboxylic acid.

17. The composition of claim 1, wherein the metal carboxylate is bismuth carboxylate and wherein the surfactant emulsifies about 50 ppm to about 1000 ppm of the hydrocarbonaceous solvent and the bismuth carboxylate in the water.

18. The composition of claim 1, wherein the dispersed phase contains about 10 percent to about 80 weight percent of the metal carboxylate.

19. A method of preparing the composition of claim 1, comprising combining (a) and (b).

20. A method of marking wood, comprising depositing a detectable amount of the composition of claim 1 in wood.

21. The method of claim 20, wherein the composition is deposited in the wood at greater than atmospheric pressure.

22. The method of claim 20, which includes drawing air from the wood by establishing a partial vacuum in or near the wood.

23. The method of claim 20, wherein the wood is Southern Yellow Pine.

24. The method of claim 20, wherein the metal carboxylate is dispersed in the wood.

25. A marked wood product obtained by the process of claim 20.

26. A method for authenticating wood, comprising:
   (a) depositing a detectable amount of the composition of claim 1 in wood; and
   (b) detecting the presence of the metal or the carboxylate anion in the wood.

27. Wood comprising the composition of claim 1.

* * * * *